United States Patent
Li et al.

(10) Patent No.: US 8,790,262 B2
(45) Date of Patent: Jul. 29, 2014

(54) METHOD FOR IMPLEMENTING AN IMAGING AND NAVIGATION SYSTEM

(75) Inventors: Dun Alex Li, Salem, NH (US); Christopher Allen Nafis, Rexford, NY (US); Douglas Glenn Wildes, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 938 days.

(21) Appl. No.: 11/862,969

(22) Filed: Sep. 27, 2007

(65) Prior Publication Data

US 2008/0287794 A1 Nov. 20, 2008

Related U.S. Application Data

(60) Provisional application No. 60/938,372, filed on May 16, 2007.

(51) Int. Cl.
*A61B 8/00* (2006.01)

(52) U.S. Cl.
USPC .......................................... 600/439; 600/437

(58) Field of Classification Search
CPC ........................................................ A61B 8/00
USPC ................................................. 600/439, 437
See application file for complete search history.

(56) References Cited

U.S. PATENT DOCUMENTS

| | | | |
|---|---|---|---|
| 6,669,635 B2 | 12/2003 | Kessman et al. | |
| 6,716,166 B2 | 4/2004 | Govari | |
| 6,773,402 B2 | 8/2004 | Govari et al. | |
| 7,090,639 B2 | 8/2006 | Govari | |
| 7,156,816 B2 | 1/2007 | Schwartz et al. | |
| 7,452,357 B2 * | 11/2008 | Vlegele et al. | 606/32 |
| 7,681,579 B2 * | 3/2010 | Schwartz | 128/898 |
| 2002/0005719 A1 | 1/2002 | Gilboa et al. | |
| 2002/0026118 A1 | 2/2002 | Govari | |
| 2002/0042571 A1 | 4/2002 | Gilboa et al. | |
| 2002/0049375 A1 | 4/2002 | Strommer et al. | |
| 2003/0013958 A1 | 1/2003 | Govari et al. | |
| 2003/0074011 A1 | 4/2003 | Gilboa et al. | |
| 2003/0208102 A1 | 11/2003 | Gilboa | |
| 2004/0102769 A1 | 5/2004 | Schwartz et al. | |
| 2004/0138548 A1 | 7/2004 | Strommer et al. | |
| 2004/0162507 A1 | 8/2004 | Govari | |
| 2004/0162550 A1 | 8/2004 | Govari et al. | |
| 2004/0254458 A1 | 12/2004 | Govari | |
| 2005/0107688 A1 | 5/2005 | Strommer | |

(Continued)

OTHER PUBLICATIONS

Kanckstedt, C. et al, "Semi-automated 3-dimensional intracardiac echocardiography: development and initial clinical experience of a new system to guide ablation procedures", Heart Rhythm, 3 (12), pp. 1453-1459, 2006.

(Continued)

*Primary Examiner* — Peter Luong
(74) *Attorney, Agent, or Firm* — Andrus Intellectual Property Law, LLP

(57) ABSTRACT

A method for implementing an imaging and navigation system to perform a medical procedure such as cardiac ablation is disclosed herein. The a method includes implementing an ultrasonic imaging device to provide a generally real time three-dimensional patient image, identifying a target site on the generally real time three-dimensional patient image, directing a medical instrument to the target site using a tracking system, and performing a medical procedure at the target site.

17 Claims, 4 Drawing Sheets

(56) References Cited

U.S. PATENT DOCUMENTS

| | | | |
|---|---|---|---|
| 2005/0197557 | A1 | 9/2005 | Strommer et al. |
| 2006/0241445 | A1 | 10/2006 | Altmann et al. |
| 2006/0253024 | A1 | 11/2006 | Altmann et al. |
| 2006/0253029 | A1 | 11/2006 | Altmann et al. |
| 2006/0253030 | A1 | 11/2006 | Altmann et al. |
| 2006/0253031 | A1 | 11/2006 | Altmann et al. |
| 2006/0253032 | A1 | 11/2006 | Altmann et al. |
| 2007/0062547 | A1* | 3/2007 | Pappone ................ 128/898 |
| 2007/0167801 | A1* | 7/2007 | Webler et al. ............ 600/459 |
| 2007/0167821 | A1 | 7/2007 | Lee et al. |

OTHER PUBLICATIONS

Proulx, T.L. et al, "Advances in Catheter-Based Ultrasound Imaging", IEEE International Ultrasonics Symposium Proceedings, 2005.

Rotger, D. et al, "Multimodal Registration of Intravascular ultrasound Images and Angiography", Computer Vision Center Universitat Autonoma de Barcelona Bellaterra, Spain, www.cvc.uab.es/~petia/caseib2002.pdf.

Huang, X. et al, "Dynamic 3D Ultrasound and MR Image Registration of the Beating Heart", MICAI, LNCS 3750, pp. 171-178, 2005.

Martin, R. et al, "A Miniature Position and Orientation Locator for Three Dimensional Echocardiography", IEEE Proceedings on Computer in Cardiology, pp. 25-28, 1993.

Beaseley, R. A. et al, "Registration of ultrasound images", www.tgt.vanderbilt.edu/archive/Registration of ultrasound images. pdf.

Leotta, D. F. et al, "Three-Dimensional Ultrasound Imaging Using Multiple Magnetic Tracking Systems and Miniature Magnetic Sensors", IEEE on Ultrasonics Symposium, pp. 1415-1418, 1995.

Pagoulatos, N. et al, "Interactive 3-D Registration of Ultrasound and Magnetic Resonance Images Based on a Magnetic Position Sensor", IEE on Info. Tech. In Biomedicine, vol. 3, No. 4, 1999.

"Catheter Ablation", Cleveland Clinic—Heart & Vascular Institute, http://www.clevelandclinic.org/heartcenter/pub/guide/tests/procedures/ablation.htm, Apr. 2005.

* cited by examiner

METHOD FOR IMPLEMENTING AN IMAGING AND NAVIGATION SYSTEM

RELATED APPLICATIONS

This application claims priority to Provisional Application No. 60/938,372 filed on May 16, 2007, and is hereby incorporated herein by reference in its entirety.

BACKGROUND OF THE INVENTION

The subject matter disclosed herein relates to a method for implementing an imaging and navigation system.

Atrial fibrillation is characterized by very rapid uncoordinated electrical signals in the atria of the heart resulting in a rapid and irregular heart beat. Atrial fibrillation can significantly impact a patient's quality of life producing symptoms such as shortness of breath, weakness, difficulty exercising, sweating, dizziness, and fainting. In some patients, atrial fibrillation can be associated with increased risk of stroke, heart failure, or heart muscle disease. It is known to treat atrial fibrillation using a process referred to as cardiac ablation wherein a small section of heart tissue is killed or otherwise rendered inactive thereby breaking the electrical pathways causing the fibrillation.

One problem with interventional procedures such as cardiac ablation is that it is difficult to precisely direct treatment to targeted anatomic regions without damaging surrounding tissue. Another problem with these procedures is that it is difficult to visualize and access appropriate anatomic regions in a minimally invasive manner such that the risk of complications and patient recovery time are minimized.

BRIEF DESCRIPTION OF THE INVENTION

The above-mentioned shortcomings, disadvantages and problems are addressed herein which will be understood by reading and understanding the following specification.

In an embodiment, a method includes implementing an ultrasonic imaging device to provide a generally real time three-dimensional patient image, identifying a target site on the generally real time three-dimensional patient image, directing a medical instrument to the target site using a tracking system, and performing a medical procedure at the target site.

In another embodiment, a method includes implementing an ultrasound catheter to provide a generally real time three-dimensional patient image, identifying a target site on the generally real time three-dimensional patient image, directing a medical instrument to the target site using a tracking system, performing a medical procedure at the target site, and implementing the ultrasound catheter to monitor the performance of the medical procedure.

In another embodiment, a method includes implementing an ICE imaging device to provide a generally real time three-dimensional patient image, identifying a plurality of target sites on the generally real time three-dimensional patient image, and selecting an optimal path to the plurality of target sites and displaying the optimal path on the generally real time three-dimensional patient image. The method also includes directing an ablation catheter along the optimal path to each of the plurality of target sites using a tracking system, implementing the ablation catheter to perform a cardiac ablation procedure at each of the plurality of target sites, implementing an ICE catheter to monitor the performance of the cardiac ablation procedure at each of the plurality of target sites, and graphically identifying each of the plurality of target sites at which the cardiac ablation procedure has been performed.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
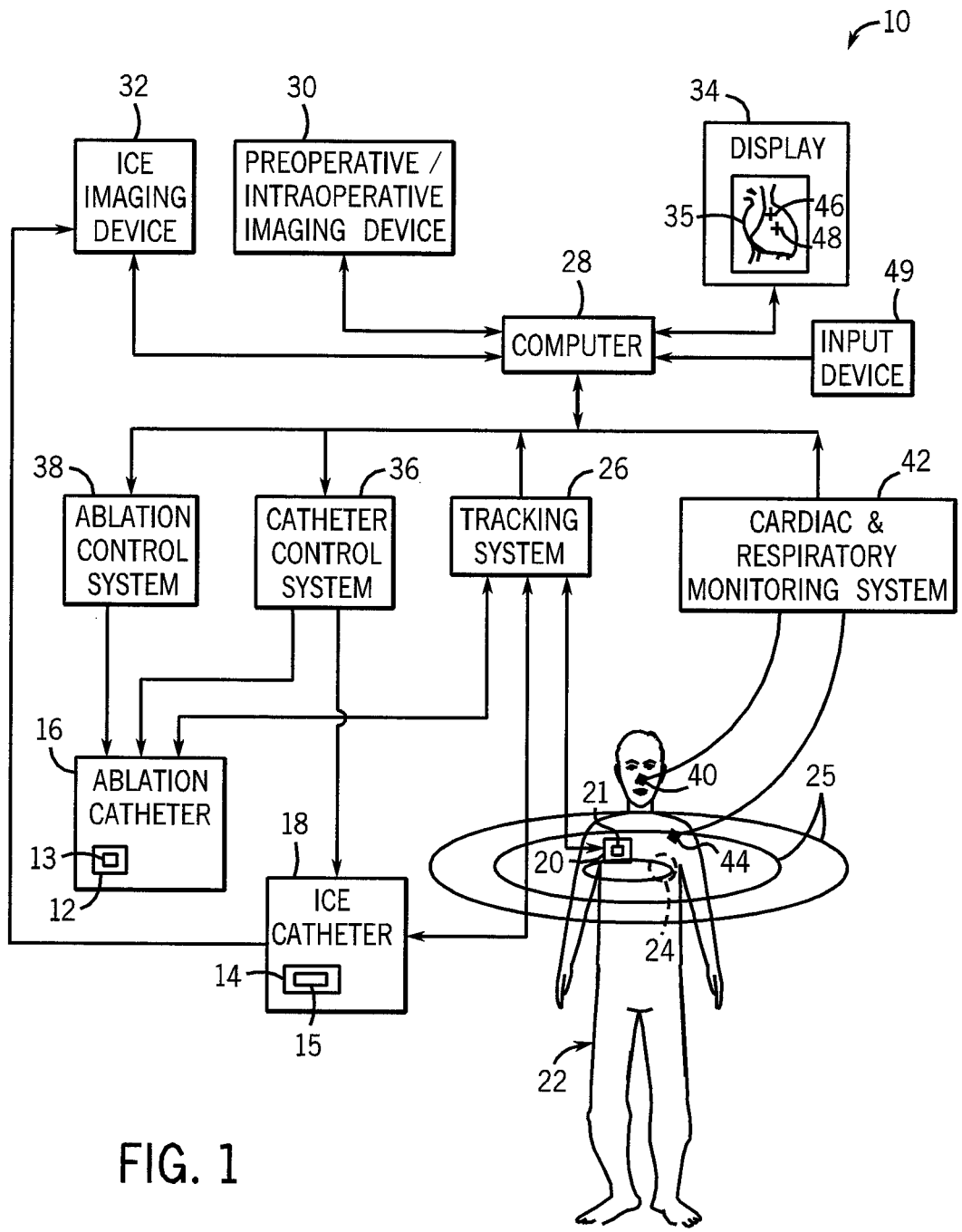
FIG. 1 is a schematic representation of an imaging and navigation system in accordance with an embodiment.

Referring to FIG. 1, a system 10 is shown in accordance with one embodiment. The system 10 will hereinafter be described as an imaging and navigation system adapted for treating atrial fibrillation using an ablation procedure. The system 10 will also hereinafter be described as implementing intracardiac echocardiography (ICE) to facilitate the performance of the ablation procedure. It should, however, be appreciated that the system 10 may also be implemented to treat other medical conditions and to perform other procedures, and that the system 10 may implement alternate ultrasonic technologies in place of ICE.

The navigation portion of the imaging and navigation system 10 includes a tracking system 26 that is operatively connected to a plurality of tracking elements 12, 14 and 20. According to one embodiment, the tracking system 26 and tracking elements 12, 14 and 20 implement electromagnetic (EM) tracking technology, however, alternate tracking technologies and/or tracking systems may be envisioned. The tracking element 12 is adapted for attachment to an ablation catheter 16, and the tracking element 14 is adapted for attachment to an ICE catheter 18. For purposes of this disclosure, a catheter is defined to include any flexible medical delivery system such as, for example, an endoscope. The tracking element 20 can be rigidly attached to an internal organ (e.g., the heart 24) or to the external body of the patient 22 in a conventional manner. A tracking element 20 secured to the patient's heart 24 may be referred to as a "dynamic reference" because it is adapted to move along with the heart 24. An exemplary method of attaching the tracking element 20 to the patient's heart 24 is through a minimally invasive procedure using a dynamic reference catheter (not shown).

The present invention will hereinafter be described in accordance with an embodiment wherein the tracking element 20 comprises a field generator 21, the tracking element 12 comprises one or more field sensors 13, and the tracking element 14 comprises one or more field sensors 15. It should, however, be appreciated that according to alternate embodiments the tracking element 20 may include a field sensor and the tracking elements 12, 14 may include field generators. The field generator 21 generates a magnetic field 25 in an area that includes the target site (e.g., the patient's heart 24). The field sensors 13, 15 are adapted to measure the magnetic field 25, and to transmit the magnetic field measurements to the tracking system 26. The tracking system 26 implements the magnetic field measurements to calculate the position and orientation of the tracking elements 12, 14. After calculating the position and orientation of the tracking elements 12, 14, the position and orientation of the ablation catheter 16 and the ICE catheter 18 respectively attached thereto can also be calculated in a known manner.

The tracking system 26 transmits the catheter position and orientation data to a computer 28. The computer 28 registers the position and orientation data to an image obtained from a preoperative/intraoperative imaging device 30 and/or to an image obtained from an ICE imaging device 32. The preoperative/intraoperative imaging system 30 may, for example, include a CT imaging device, a MR imaging device, a PET imaging device, an ultrasound imaging device, an X-ray imaging device, or any other known imaging device, as well as any combinations thereof. The preoperative/intraoperative imaging device 30 may provide 2D, 3D or 4D images. For purposes of this disclosure, 4D refers to the three primary dimensions (i.e., as measured along X, Y and Z axes) and the fourth dimension which is time. Therefore, for purposes of this disclosure, 4D is synonymous with generally real time 3D. Also for purposes of this disclosure, a generally real time image includes a maximum image delay of approximately one second. The ICE imaging device 32 is configured to obtain imaging data from the ICE catheter 18 and produce 2D, 3D or 4D images as will be described in detail hereinafter.

The catheter position and orientation data can be visualized on the display 34. According to one embodiment, graphic representations corresponding to the ablation catheter 16 and the ICE catheter 18 may be virtually superimposed on a patient image 35. In the embodiment of FIG. 1, the graphic representations corresponding to the catheters 16, 18 include the cross-hairs 46, 48 respectively representing the distal end portions of the ablation catheter 16 and the ICE catheter 18, however other embodiments may include a more complete rendering showing the catheters 16, 18 in detail. In a non-limiting manner, the patient image 35 may include a CT image, a MR image, a PET image, an ultrasound image or an X-ray image from the preoperative/intraoperative imaging device 30. The patient image 35 may also include a real time 3D image from the ICE imaging device 32, or a fused image comprising a plurality of images from the preoperative/intraoperative imaging device 30 and/or the ICE imaging device 32 that have been combined in a known manner.

The input device 49 may include any known apparatus or system such as a keyboard, mouse, touch screen, joystick, etc., and is generally adapted to allow a user to manually input data into the system 10. Although shown in FIG. 1 as a separate component, the input device 49 may alternatively be incorporated into one of the other system 10 components such as the computer 28 or the display 34. As an example, the input device 49 may include a touch screen device integrated into the design of the display 34 and adapted to facilitate surgical planning. According to one embodiment, the exemplary touch screen input device 49 could be implemented to highlight or otherwise identify specific regions of interest on a patient image obtained from one of the imaging devices 30, 32. According to another embodiment, the exemplary touch screen input device 49 could be implemented to assign a priority sequence to a plurality of regions of interest.

A catheter control system 36 is operatively connected to both the ablation catheter 16 and the ICE catheter 18. The catheter control system 36 is adapted to translate and steer the catheters 16, 18 through the patient 22 to a predefined destination at or near the patient's heart 24. The catheter control system 36 may be configured to translate and steer the catheters 16, 18 in response to manual operator inputs, or may be configured to automatically direct the catheters 16, 18 to a selectable target site. The catheter control system 36 may also be operatively connected to and configured to control a dynamic reference catheter (not shown) adapted to facilitate the attachment of the tracking element 20 to the patient's heart 24.

An ablation control system 38 controls the energy transfer to the ablation catheter 16. Accordingly, when an operator determines that the distal end of the ablation catheter 16 is in sufficiently close proximity to a targeted cardiac region, the ablation control system 38 can be implemented to transmit a selectable amount of energy. The transmission of energy in this manner kills or otherwise renders inactive the targeted region in order to break electrical pathways causing atrial fibrillation. In a non-limiting manner, the ablation control system 38 may implement radio frequency (RF), cryogenic, ultrasound, or laser technologies.

One or more respiratory sensors 40 can be positioned near the patient's mouth and/or nose in order to monitor respiration, and one or more cardiac sensors 44 can be positioned near the patient's heart 24 to monitor cardiac activity. The respiratory sensors 40 and the cardiac sensors 44 are operatively associated with and adapted to transmit sensor data to a monitoring system 42. Any sensor data collected by the monitoring system 42 is transferable to the computer 28 such that the computer 28 may be implemented to synchronize the operation of the tracking system 26, the imaging device 30, and/or the imaging device 32 with the patient's cardiac and respiratory activity. According to one example, the computer 28 may implement data from the monitoring system 42 to acquire images during predefined portions of a patient's cardiac or respiratory cycle. According to another example, the computer 28 may implement data from the monitoring system 42 to sequence a series of 2D images or slices in a manner that corresponds with a patient's cardiac or respiratory cycle in order to provide a generally real time rendering of a dynamic object such as the patient's heart 24.

Figure 2:
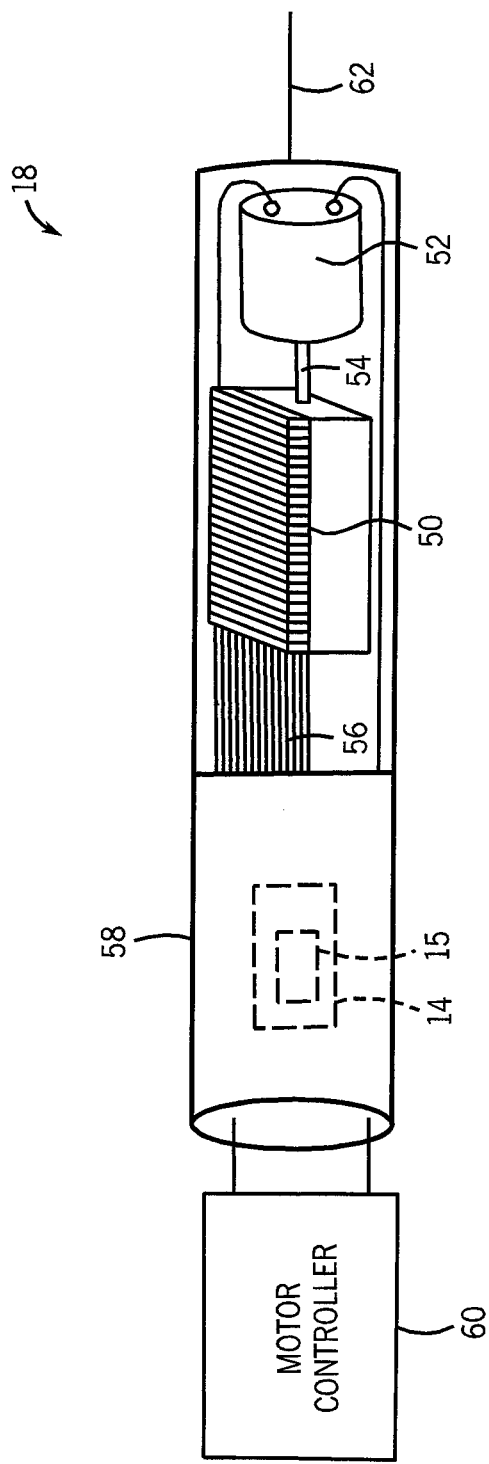
FIG. 2 is a partially cutaway schematic illustration of an ICE catheter in accordance with an embodiment.

Referring to FIG. 2, a more detailed illustration of the ICE catheter 18 is shown. The ICE catheter 18 will hereinafter be described in detail in accordance with an embodiment. It should, however, be appreciated that the ICE catheter 18 may be replaced with a similar catheter system adapted to retain any known ultrasonic imaging device.

The ICE catheter 18 comprises a transducer array 50, a motor 52, which may be internal or external to the space-critical environment, a drive shaft 54 or other mechanical connections between motor 52 and the transducer array 50, and an interconnect 56. The ICE catheter 18 further includes a catheter housing 58 enclosing the transducer array 50, motor 52, interconnect 56 and drive shaft 54. In the depicted embodiment, the transducer array 50 is mounted on drive shaft 54 and the transducer array 50 is rotatable with the drive shaft 54. The rotational motion of the transducer array 50 is controlled by motor controller 60 and motor 52. Interconnect 56 refers to, for example, cables and other connections coupling the transducer array 50 with the ICE imaging device 32 (shown in FIG. 1) for use in receiving and/or transmitting signals therebetween. In an embodiment, interconnect 56 is configured to reduce its respective torque load on the transducer array 50 and motor 52. The catheter housing 58 is of a material, size and shape adaptable for internal imaging applications and insertion into regions of interest. According to the embodiment depicted in FIG. 2, the catheter housing 58 is generally cylindrical defining a longitudinal axis 62.

The catheter housing 58, or at least the portion that intersects the ultrasound imaging volume, is acoustically transparent, e.g. low attenuation and scattering, acoustic impedance near that of blood and tissue (Z~1.5M Rayl). The space between the transducer and the housing can be filled with an acoustic coupling fluid (not shown), e.g., water, with acoustic impedance and sound velocity near those of blood and tissue (Z~1.5 M Rayl, V~1540 m/sec).

According to one embodiment, the transducer array 50 is a 64-element one-dimensional array having 0.110 mm azimuth pitch, 2.5 mm elevation and 6.5 MHz center frequency. The elements of the transducer array 50 are electronically phased in order to acquire a sector image parallel to the longitudinal axis 62 of the catheter housing 58. The transducer array 50 is mechanically rotated about the longitudinal axis 62 to image a three-dimensional volume. The transducer array 50 captures a plurality of two-dimensional images as it is being rotated. The plurality of two-dimensional images are transmitted to the ICE imaging device 32 (shown in FIG. 1) which is configured to sequentially assemble the two-dimensional images in order to produce a three-dimensional image.

The rate at which the transducer array 50 is rotated about the longitudinal axis 62 can be regulated by the motor controller 60. The transducer array 50 can be rotated relatively slowly to produce a 3D image, or relatively quickly to produce a generally real time 3D image (i.e., a 4D image). The motor controller 60 is also operable to vary the direction of rotation to produce an oscillatory transducer array motion. In this manner, the range of motion and imaged volume are restricted such that the transducer array 50 can focus on imaging a specific region and can update the 3D image of that region more frequently, thereby providing a real-time 3D, or 4D, image.

Referring to FIGS. 1 and 2, an embodiment of the ICE catheter 18 includes an integrally attached tracking element 14 disposed within the catheter housing 58. The integrally attached tracking element 14 is adapted to work in combination with the tracking element 20 and the tracking system 26 to estimate the position and/or orientation of the ICE catheter 18. As previously described, the tracking element 14 may comprise either the field sensor 15 or a field generator (not shown) similar to the field generator 21.

It should be appreciated by those skilled in the art that the previously described ICE catheter 18 is a single embodiment, and that alternate configurations may be envisioned. For example, the transducer array 50, motor 52 and drive shaft 54 define a mechanical 4D ICE embodiment that could be replaced by a functionally equivalent electrical 4D ICE embodiment (not shown). The electrical 4D ICE embodiment may, for example, comprise a 2D matrix transducer array (not shown) integrated with an electronic device (not shown) configured to steer the ultrasound beam in azimuth and elevation. In this manner, the electrical 4D ICE embodiment could image a 3D or 4D volume without necessarily moving the transducer array.

Figure 3:
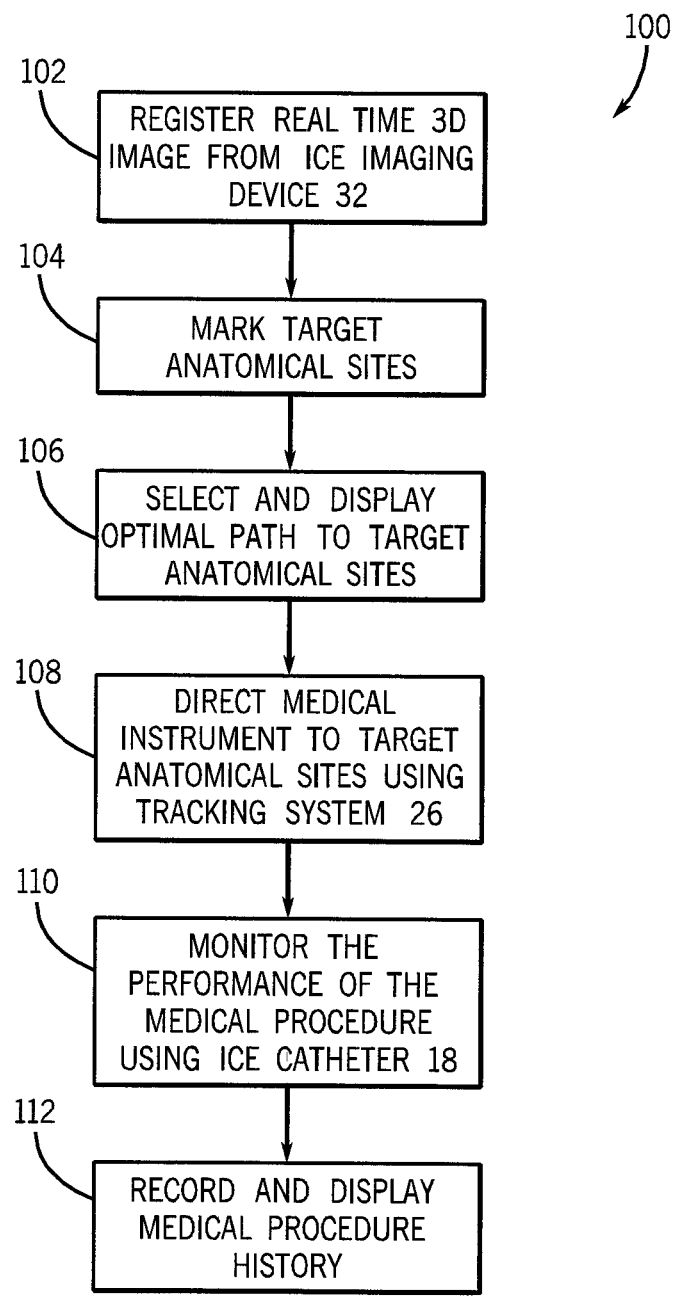
FIG. 3 is a flow chart illustrating a method in accordance with an embodiment.

Referring to FIG. 3, a block diagram illustrates a method 100. The technical effect of the method 100 is to provide visual information pertaining to the performance of a medical procedure that is observable on a display. According to an exemplary embodiment, the method 100 may be applied to perform a cardiac ablation procedure, however, it should be appreciated that the method 100 may also be applied to perform other medical procedures. The individual blocks shown in FIG. 3 represent steps that may be performed in accordance with the method 100.

Referring to FIGS. 1 and 3, at step 102 a real time 2D or 3D image from the ICE imaging system 32 is registered. For purposes of this disclosure, the term "register" refers to the process of spatially identifying and coordinating common reference points in data obtained from the tracking system 26, the imaging device 30 and/or the imaging device 32. For example, a real time 3D image from the ICE imaging device 32 may be registered with position and orientation data from the tracking system 26 in order to ensure that a graphical representation of a tracked instrument is superimposed onto an appropriate region of the real time 3D image. A real time 3D image from the ICE imaging device 32 may also be registered with an image from the preoperative/intraoperative imaging device 30 to produce a fusion or composite image comprising data from both devices 30, 32.

Figure 4:
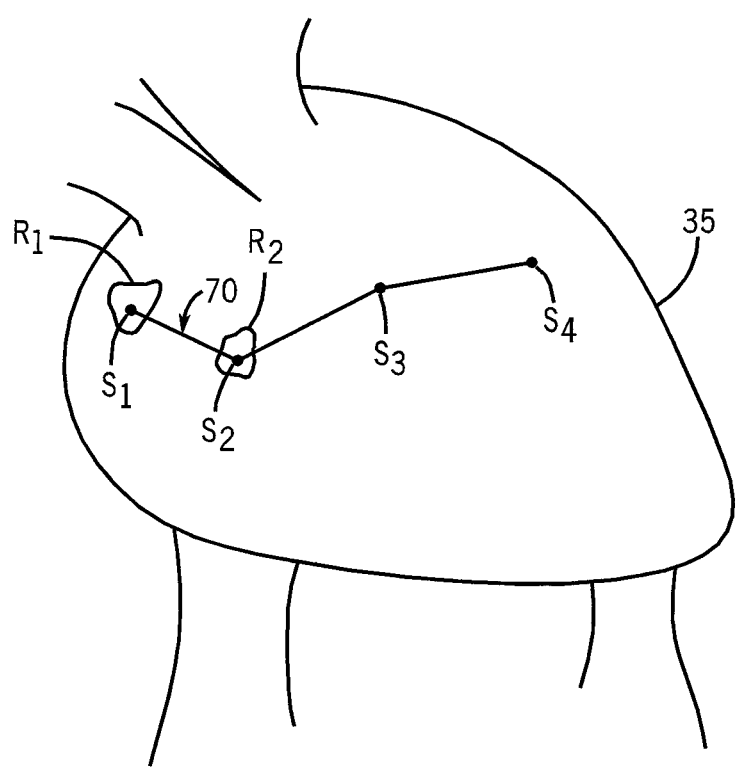
FIG. 4 is a detailed schematic illustration of a patient image with superimposed target sites and optimal path.

FIG. 4 is a more detailed depiction of the patient image 35 shown in accordance with an embodiment. Referring now to FIGS. 3 and 4, at step 104 of the method 100 predetermined regions or sites such as the exemplary target anatomical sites S1-S4 are marked or otherwise identified on the patient image 35. According to the embodiment wherein the method 100 is applied to perform a cardiac ablation procedure, the target anatomical sites S1-S4 may include sections of heart tissue to be rendered inactive in order to break electrical pathways causing atrial fibrillation. The process of marking the target anatomical sites S1-S4 may include identifying specific portions or regions of the patient image 35 such as, for example, by highlighting the regions, coloring the regions, or otherwise graphically indicating the target anatomical sites S1-S4.

At step 106, the computer 28 (shown in FIG. 1) selects an optimal path 70 to the target anatomical sites S1-S4 based on feedback from one or more of the tracking system 26, the imaging device 30, and the imaging device 32 (shown in FIG. 1). Alternatively, the selection of an optimal path 70 may be manually performed or may comprise user-guided path planning. The selection of an optimal path is well known to those skilled in the art and will therefore not be described in detail. After selecting the optimal path 70, the path 70 can be graphically depicted by the display 34 (shown in FIG. 1). The optimal path 70 may, for example, be depicted by a colored or highlighted line superimposed onto the patient image 35.

At step 108, a medical instrument is directed along the optimal path 70 to each of the target anatomical sites S1-S4. The medical instrument directed along the optimal path 70 will hereinafter be described as the ablation catheter 16 (shown in FIG. 1), however it should be appreciated that other instruments may be envisioned. According to one embodiment, an operator may implement the catheter control system 36 (shown in FIG. 1) to manually direct the ablation catheter 16 along the optimal path 70 to the target anatomical sites S1-S4. The tracking system 26 and display 34 (shown in FIG. 1) may be implemented to facilitate the manual direction of the ablation catheter 16 along the optimal path 70 such as, for example, by generally simultaneously depicting both the optimal path 70 and the graphical representation 46 (shown in FIG. 1) of the ablation catheter 16 during the course of a given medical procedure. According to another embodiment, the catheter control system 36 can be implemented to automatically direct the ablation catheter 16 along the optimal path 70 and to the target anatomical sites S1-S4.

Referring now to FIGS. 1 and 3, at step 110 the performance of the medical procedure is monitored using the ICE catheter 18. The medical procedure monitored at step 110 will hereinafter be described as a cardiac ablation procedure, however it should be appreciated that other procedures may be envisioned. According to one embodiment, an operator may implement the catheter control system 36 to manually steer the ICE catheter 18 such that the ICE catheter 18 is aimed at the distal tip of the ablation catheter 16. In this manner, a surgeon can monitor a real time 2D or 3D patient image from the ICE imaging device 32 in order to observe the ablation procedure as it is being performed. The tracking system 26 and display 34 may be implemented to facilitate the process of manually steering the ICE catheter 18 such that it remains aimed at the ablation catheter 16. As an example, the display 34 may graphically convey the position of the ablation catheter 16 and the orientation of the ICE catheter 18 to help the operator maintain optimal ICE catheter 18 orientation relative to the ablation catheter 16.

According to another embodiment, at step 110, the computer 28 and catheter control system 36 may operate in combination to steer the ICE catheter 18 such that the ICE catheter 18 automatically follows and remains aimed at the distal end of the ablation catheter 16.

According to another embodiment, at step 110, the computer 28 and the ICE imaging device 32 may operate in combination to produce a generally real time 3D patient image 35 that tracks the movement of the ablation catheter 16 in order to more conveniently monitor the cardiac ablation procedure. As an example, the generally real time 3D patient image 35 could be adapted to continuously track ablation catheter 16 movement such that the ablation catheter 16 is always centered in the field of view. The generally real time 3D patient image 35 may be rendered as a surface image or as a transparent solid image in order to more clearly show the graphical depiction 46 of the ablation catheter 16 as the patient image 35 tracks ablation catheter movement. Alternatively, the generally real time 3D patient image 35 could be stabilized to the anatomy such that ablation catheter movement is observable within the field of view.

Referring again to FIGS. 3 and 4, at step 112 medical procedure history is recorded and displayed. The medical procedure history of step 112 will hereinafter be described as a cardiac ablation history, however it should be appreciated that other procedures may be envisioned. According to one embodiment, at step 112, the computer 28 (shown in FIG. 1) records cardiac regions that have already been treated and visually conveys this information by highlighting the corresponding regions R1-R2 on the patient image 35. In this manner an operator can readily see which cardiac regions have been treated, and is therefore less likely to unintentionally revisit a target site S1-S2 that has already been addressed.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A method comprising:
    implementing an ultrasonic imaging device to provide a generally real time three-dimensional patient image;
    identifying a plurality of target sites on the generally real time three-dimensional patient image;
    directing an ablation catheter to the plurality of target sites using a tracking system;
    selecting an optimal path, wherein the optimal path begins at a first one of the plurality of target sites and includes each of the plurality of target sites;
    displaying the optimal path including each of the plurality of target sites on the generally real time three-dimensional patient image;
    directing the ablation catheter along the optimal path to each of the plurality of target sites using the tracking system;
    implementing the ablation catheter to perform a cardiac ablation procedure at each of the plurality of target sites and sensing when the ablation procedure is completed at each of the plurality of target sites; and
    highlighting in real time each of the plurality of target sites at which the cardiac ablation procedure has been performed by highlighting those target sites at which the ablation procedure has been performed as the ablation procedure is completed at each of the plurality of target sites wherein the highlighting in real time is triggered and the completion of the ablation procedure is marked at each of the plurality of target sites by the sensing when the ablation procedure is completed, thus highlighting the progress of the ablation catheter along the optimal path by highlighting a portion of the optimal path that has been completed.

2. The method of claim 1, wherein said implementing an ultrasonic imaging device to provide a generally real time three-dimensional patient image comprises implementing the ultrasonic imaging device in combination with a second imaging device to provide a composite generally real time three-dimensional patient image.

3. The method of claim 1, wherein said implementing an ultrasonic imaging device to provide a generally real time three-dimensional patient image comprises implementing the ultrasonic imaging device to provide a surface patient image or a transparent solid patient image.

4. The method of claim 1, further comprising implementing an ultrasound catheter to monitor the performance of the cardiac ablation procedure.

5. The method of claim 4, wherein said implementing the ultrasound catheter to monitor the performance of the cardiac ablation procedure includes implementing the tracking system to identify a position and/or orientation of the ultrasound catheter.

6. The method of claim 1, further comprising highlighting each of the plurality of target sites on the generally real time three-dimensional patient image after performing the medical procedure.

7. The method of claim 1, wherein said implementing an ultrasonic imaging device comprises implementing an ICE imaging device.

8. A method comprising:
    implementing an ultrasound catheter to provide a generally real time three-dimensional patient image;
    identifying a plurality of target sites on the generally real time three-dimensional patient image;
    directing an ablation catheter to the plurality of target sites using a tracking system;
    selecting an optimal path, wherein the optimal path begins at a first one of the plurality of target sites and includes each of the plurality of target sites;
    displaying the optimal path including each of the plurality of target sites on the generally real time three-dimensional patient image;
    directing the ablation catheter along the optimal path to each of the plurality of target sites using the tracking system;
    implementing the ablation catheter to perform a cardiac ablation procedure at each of the plurality of target sites and sensing when the ablation procedure is completed at each of the plurality of target sites;
implementing the ultrasound catheter to monitor the performance of the cardiac ablation procedure; and
highlighting in real time each of the plurality of target sites at which the cardiac ablation procedure has been performed by highlighting those target sites at which the ablation procedure has been performed as the ablation procedure is completed at each of the plurality of target sites wherein the highlighting in real time is triggered and the completion of the ablation procedure is marked at each of the plurality of target sites by the sensing when the ablation procedure is completed, thus highlighting the progress of the ablation catheter along the optimal path by highlighting a portion of the optimal path that has been completed.

9. The method of claim 8, wherein said implementing an ultrasound catheter to provide the generally real time three-dimensional patient image comprises implementing the ultrasound catheter in combination with a second imaging device to provide a composite generally real time three-dimensional patient image.

10. The method of claim 8, wherein said implementing an ultrasound catheter to provide the generally real time three-dimensional patient image comprises implementing the ultrasound catheter to provide a surface patient image or a transparent solid patient image.

11. The method of claim 8, wherein said directing the ablation catheter to each of the plurality of target sites comprises directing the ablation catheter to the target site using the tracking system, wherein the tracking system is an electromagnetic tracking system.

12. The method of claim 8, wherein said directing the ablation catheter to each of the plurality of target sites comprises automatically directing the ablation catheter to each of the plurality of target sites using the tracking system in combination with a catheter control system.

13. The method of claim 8, further comprising highlighting each of the plurality of target sites on the generally real time three-dimensional patient image after performing the cardiac ablation procedure.

14. A method comprising:
implementing an ICE imaging device to provide a generally real time three-dimensional patient image;
identifying a plurality of target sites on the generally real time three-dimensional patient image;
selecting an optimal path, wherein the optimal path begins at a first one of the plurality of target sites and includes each of the plurality of target sites;
displaying the optimal path including each of the plurality of target sites on the generally real time three-dimensional patient image;
directing an ablation catheter along the optimal path to each of the plurality of target sites using a tracking system;
implementing the ablation catheter to perform a cardiac ablation procedure at each of the plurality of target sites and sensing when the ablation procedure is completed at each of the plurality of target sites;
implementing an ICE catheter to monitor the performance of the cardiac ablation procedure at each of the plurality of target sites; and
highlighting in real time each of the plurality of target sites at which the cardiac ablation procedure has been performed highlighting those target sites at which the ablation procedure has been performed as the ablation procedure is completed at each of the plurality of target sites wherein the highlighting in real time is triggered and the completion of the ablation procedure is marked at each of the plurality of target sites by the sensing when the ablation procedure is completed, thus highlighting the progress of the ablation catheter along the optimal path by highlighting a portion of the optimal path that has been completed.

15. The method of claim 14, wherein said implementing an ICE imaging device to provide the generally real time three-dimensional patient image comprises implementing the ICE imaging device in combination with a second imaging device to provide a composite generally real time three-dimensional patient image.

16. The method of claim 14, wherein said directing the ablation catheter along the optimal path comprises automatically directing the ablation catheter along the optimal path using the tracking system in combination with a catheter control system.

17. The method of claim 14, wherein said implementing the ICE catheter to monitor the performance of the cardiac ablation procedure includes implementing, the tracking system to identify a position and/or orientation of the ICE catheter.

* * * * *